June 24, 1952 E. G. FISHER Plant Pat. 1,109
ROSE PLANT
Filed April 9, 1951
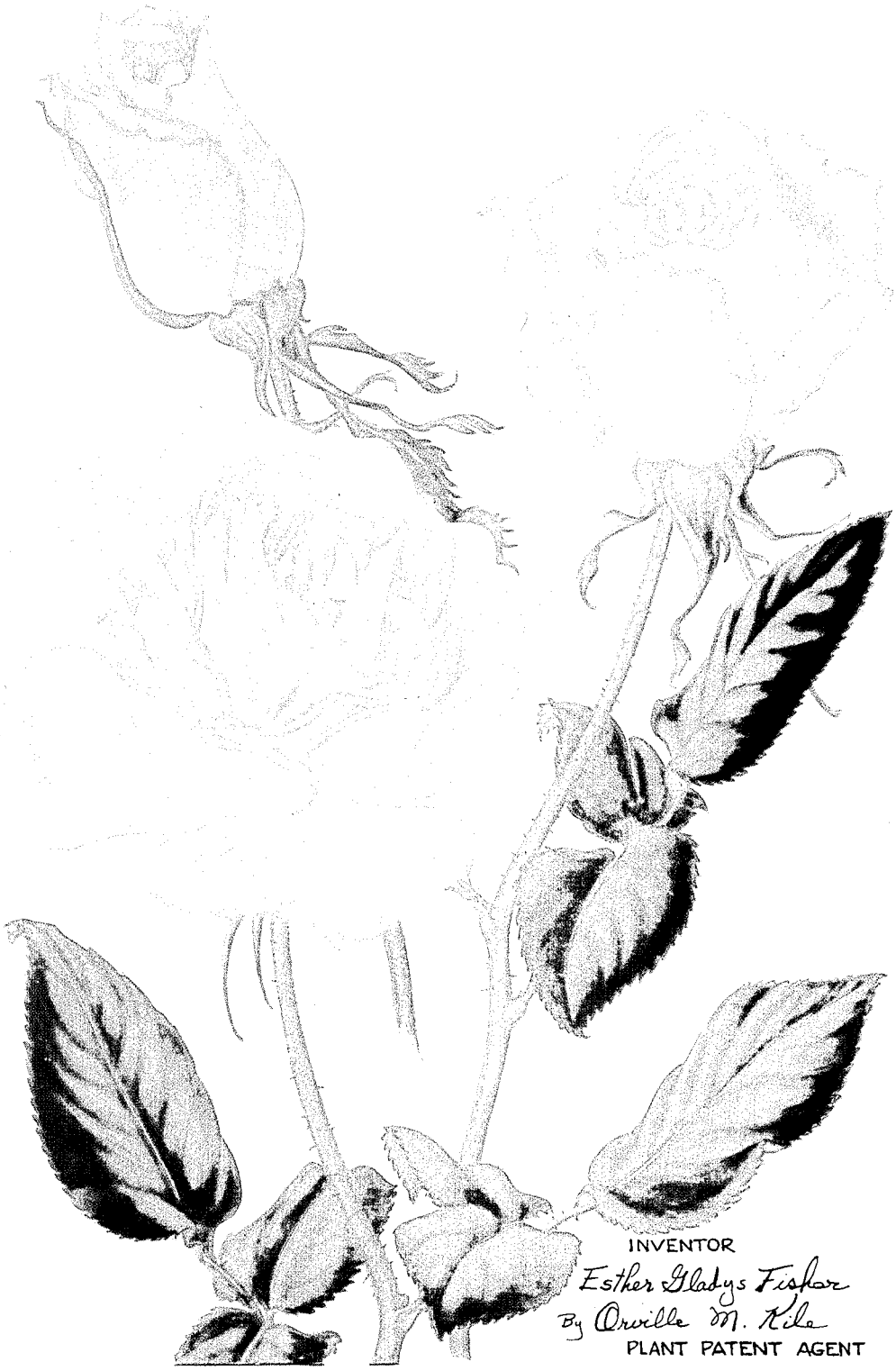
INVENTOR
Esther Gladys Fisher
By Orville M. Kile
PLANT PATENT AGENT Patented June 24, 1952

Plant Pat. 1,109

UNITED STATES PATENT OFFICE 1,109

ROSE PLANT

Esther Gladys Fisher, Woburn, Mass., assignor to
Arnold-Fisher Company, Woburn, Mass.

Application April 9, 1951, Serial No. 220,105

1 Claim. (Cl. 47—61)

My present invention relates to a new and distinct variety of hybrid tea rose plant of the multicolor class. It resulted from a cross between the varities Peace (Plant Patent No. 591) and Orange Nassau (Plant Patent No. 350), made by me at Woburn, Massachusetts. It has been asexually reproduced by me at the some location, by grafting and budding, and its outstanding characteristics appear to be permanent.

The new variety has some of the characteristics of each parent, having, among other things, taken the shape and substance of its flower from Peace and some of its coloring from Orange Nassau. In coloring, its bud somewhat resembles Talisman (unpatented) although in later stages of opening it turns to a deep rose pink on the inner surface with a creamy yellow outer surface, thus producing a bi-color effect.

One outstanding feature of the variety is that it seems to grow equally well indoors and outdoors, although we consider it essentially a greenhouse rose and the plants under test are now under greenhouse culture. Unlike many varieties, this new variety produces flowers continuously throughout the winter months in the greenhouse. The variety reproduces easily and apparently is disease-free.

The accompanying illustration represents three typical specimens of this new variety in various stages of opening, in as true colors as the artist could show them. In a later stage of opening the color is lighter and the petals reflex, showing little of their outer surface. It must be pointed out that the shadings and combination of coloring varies greatly in various specimens of this variety.

In the following detailed description, color plate references are to Ridgway's Color Standards and Nomenclature, while for other colors the ordinary dictionary meaning is intended.

*The plant*

Growth habit: Upright bush, moderately branched, attaining a height of 5 to 6 feet as grown in the greenhouse. It is an excellent, free grower although not rank in growth. Reproduction both by grafting and by budding has proved almost 100% successful, this ease of reproduction adding greatly to the value of the plant for greenhouse use.

Blooming habit: Splendid producer of good blooms. Unlike most rose varieties, the plants under test produce flowers continuously throughout the winter months in our greenhouses.

Stems:

*Size.*—Usually 18 to 20 inches in length, and moderately heavy.

*Strength.*—Strong and upright.

*Color.*—Cerro Green (Plate V) to Olive Green (Plate IV), considerably tinged with red in the stronger plants.

*Thorns.*—Many; irregularly spaced and sized; sharp-pointed and slender; outward and slightly downward pointing; rose pink at base with light green tips.

*Prickles.*—Many, occurring along stem irregularly between thorns, on peduncle, and on under side of rachis.

*Internodes.*—Average length.

Foliage:

*Type.*—3 to 5 leaflets.

*Quantity.*—Abundant. Frequently 2 or 3 leaves spring from the same axil bud.

*Size.*—Medium to large. The larger terminal leaflets are about 4 inches long by 2¼ inches wide.

*Texture.*—Substantial but soft to touch.

*Aspect.*—Dull sheen. Veins prominent.

*Shape.*—Elliptical, with rounded base and acuminate apex. Edge sharply crenate.

*Color.*—Upper surface is approximately Elm Green (Plate XVII), often even brighter. The undersurface is approximately Light Elm Green (Plate XVII). Edge red in the stronger plants.

*Rachis.*—Long; slender; sometimes has portion tinged with red; tiny thorns usually found on under side.

*Stipules.*—Very narrow; short; points acute.

*Disease resistance.*—This variety has been completely free from disease as grown in the greenhouse.

*Bloom*

Bud:

*Peduncle.*—Medium length; covered with prickles; strong; erect; approximately Parrot Green (Plate VI).

*Size.*—Medium, measuring 1½ to 1¾ inches just before expanding.

*Form.*—Ovoid, opening high-centered.

*Color.*—With combination of colors somewhat resembling that of the Talisman bud, the outside of the petals being deep yellow—Wax Yellow to Mustard Yellow (Plate XVI) at the base, tempered with orange-rose tints on the remainder of the surface except a narrow rim which ranges from deep orange-rose to approximately Tyrian Rose (Plate XII) and in some cases approximately crimson. Inner surface of petal varies in different specimens from deep salmon-rose to Tyrian Rose (Plate XII), with a deep yellow aiglet which is approximately Lemon Chrome (Plate IV).

*Opening.*—Bud opens well regardless of weather conditions.

Bloom:

*Borne.*—Singly.

*Size.*—Large. When fully open, the best blooms are 5 to 5½ inches in diameter.

*Form.*—Much like that of its parent Peace (Plant Patent 591), having high center with effect of great depth in the opening rose, outer petals reflexing or curving backward in a graceful manner. A distinct whorl is evident while the rose is unfolding. The newly open flower shows the center somewhat, but as the flower ages the petals fluff up and largely cover the pistils and stamens, particularly in the larger flowers although petals in the smaller flower lie much closer together. In a later stage the flowers open cupshaped, revealing the large center of pistils and stamens.

*Petalage.*—About 35 to 45 petals in the winter months.

*Color.*—Color combinations and changes in different specimens vary greatly although all fall within the same general color range. In a typical partly-opened rose the petals are Tyrian Rose to Rose Red (Plate XII), usually overlaid with color from Begonia Rose to Peach Red (Plate I) on the inner surface, with a large aiglet of bright yellow, approximately Lemon Chrome (Plate IV). The outer surface in the first opening stage is approximately like that of the bud. In many specimens the three outer petals have a wide streak extending through the center of the petal upward from the yellow aiglet.

About the second day much of the Begonia Rose to Peach Red (Plate I) has disappeared from the inner surface, and the outer surface colors range from an aiglet of Wax Yellow (Plate XVI) through Mustard Yellow (Plate XVI), blending into Deep Rose Pink to Rose Red (Plate XII) at the very edge or rim of the petal. Some specimens might not change so quickly.

Later the rose color is between Spinel Pink (Plate XXVI) and Rose Color (Plate XII) on the inner surface, with the outer surface colors slightly lightened.

On about the fourth day the inner surface of the petals has changed to a soft rose color between Tyrian Pink (Plate XII) and Deep Rose Pink (Plate XII), and the outer surface color lightened to approximately Colonial Buff (Plate XXX) fusing into the faint rose color of the rim.

This rose variety is a near bi-color in the bud and early stages of opening. When wide open it looks much like a pink rose because the petals fluff up and their reverse side is little in evidence.

It must be emphasized that the coloring of this rose varies considerably between specimens and in various stages of opening.

Petals:

*Shape.*—Outer petals are almost round, with slight cleft at tip of some of them. Margin otherwise whole and sometimes slightly undulate. Inner petals are much narrower and the central petals are informal and ragged.

*Texture.*—Substantial.

*Aspect.*—Silky. Inside shiny and brilliant at first, becoming dull as the flower ages.

*Size.*—Size of petals varies in different blooms. In the larger ones the petals are 2¾ inches in length and 2⅜ inches in transverse diameter.

*Fragrance.*—Moderate; spicy.

*Persistence.*—Clinging until dry.

Reproductive organs:

*Pistils.*—Many; short and even; tightly bunched in center. Styles—light yellow at base and red for the greater part of their length. Stigmas—yellow.

*Stamens.* — Many; closely surrounding bunched pistils. Filaments—slender, in most specimens short and red. Anthers—large, approximately Primuline Yellow (Plate XVI).

*Pollen.*—Abundant; golden yellow.

*Fruit.*—Hips medium in size, containing many seeds.

Having thus disclosed my invention, I claim:

The new and distinct variety of hybrid tea rose plant with features in combination approximately as herein shown and described, characterized particularly by its continuous production of good quality flowers throughout the winter in the greenhouse; its adaptability to both outdoor and greenhouse culture; its strong and healthy growth; its ease and high percentage of reproduction; the fluffy shape and good substance of its flower; and the distinctive pink to orange coloring of its bud and flower as described.

ESTHER GLADYS FISHER.

No references cited.